(12) United States Patent
Lambert et al.

(10) Patent No.: US 10,354,138 B2
(45) Date of Patent: Jul. 16, 2019

(54) REMOTE VISUAL INSPECTION SYSTEM AND METHOD

(71) Applicants: COLLINEO INC., Boucherville (CA); INNERGEX CARTIER ÉNERGIE SEC, Longueuil (CA)

(72) Inventors: Guillaume Lambert, Otterburn Park (CA); Matias Arbeleche, St-Jean-sur-Richelieu (CA); Jean-Christophe Demers, Montreal (CA); Nicolas Morency; Germain Bélanger, St-Germain de Grantham (CA); Guillaume Huet, Gaspé (CA)

(73) Assignees: COLLINEO INC., Boucherville (CA); INNERGEX CARTIER ÉNERGIE SEC, Longueuil (CA)

( * ) Notice: Subject to any disclaimer, the term of this patent is extended or adjusted under 35 U.S.C. 154(b) by 228 days.

(21) Appl. No.: 14/408,901

(22) PCT Filed: Jun. 18, 2013

(86) PCT No.: PCT/CA2013/050466
§ 371 (c)(1),
(2) Date: Dec. 17, 2014

(87) PCT Pub. No.: WO2013/188972
PCT Pub. Date: Dec. 27, 2013

(65) Prior Publication Data
US 2015/0324643 A1    Nov. 12, 2015

Related U.S. Application Data

(60) Provisional application No. 61/660,935, filed on Jun. 18, 2012, provisional application No. 61/661,875, filed on Jun. 20, 2012.

(51) Int. Cl.
*G06K 9/00* (2006.01)
*G06T 7/20* (2017.01)
(Continued)

(52) U.S. Cl.
CPC ....... *G06K 9/00637* (2013.01); *G01M 5/0091* (2013.01); *G01M 11/081* (2013.01);
(Continued)

(58) Field of Classification Search
CPC .. H04N 7/181; H04N 5/2254; H04N 13/0217; H04N 2005/2255; H04N 5/232;
(Continued)

(56) References Cited

U.S. PATENT DOCUMENTS

| 4,400,066 A | 8/1983 | Byers |
| 4,671,130 A | 6/1987 | Byers |

(Continued)

FOREIGN PATENT DOCUMENTS

| DE | 20309703 | 10/2003 |
| EP | 1869396 B1 | 12/2008 |

(Continued)

*Primary Examiner* — Thai Q Tran
*Assistant Examiner* — Syed Y Hasan
(74) *Attorney, Agent, or Firm* — Gwendoline Bruneau (57) ABSTRACT

A method and a system for remote visual inspection of a target surface of a structure, the system comprising a multi-axis assembly; a combination of dynamic digital video cameras and optic supported by said multi-axis assembly; and a controller connected to the cameras and the multi-axis assembly; wherein the multi-axis assembly comprises a turret along a vertical axis, the turret being connected at a top part thereof to a first arm extending along a roll axis, the first arm being connected to a second arm along a pitch axis, the cameras and optic being carried by the second arm.

9 Claims, 10 Drawing Sheets

US 10,354,138 B2
Page 2

(51) Int. Cl.
*G01N 21/88* (2006.01)
*G01M 5/00* (2006.01)
*G01M 11/08* (2006.01)
*G01B 11/00* (2006.01)
*G08B 13/196* (2006.01)
*B25J 9/16* (2006.01)
*H04N 5/232* (2006.01)
*H04N 5/247* (2006.01)
*H04N 5/225* (2006.01)

(52) U.S. Cl.
CPC ......... *G01N 21/88* (2013.01); *G06K 9/00664* (2013.01); *G06T 7/20* (2013.01); *H04N 5/2253* (2013.01); *H04N 5/23238* (2013.01); *H04N 5/23293* (2013.01); *H04N 5/247* (2013.01); *B25J 9/1697* (2013.01); *G01B 11/00* (2013.01); *G01N 2021/8867* (2013.01); *G01N 2021/8874* (2013.01); *G08B 13/19663* (2013.01); *Y02B 10/30* (2013.01)

(58) Field of Classification Search
CPC ...... B25J 9/1697; G01B 11/00; G01B 11/002; G01B 11/026; G01N 29/265; G06T 1/0014; G06T 7/004; G08B 13/19663; G01C 11/026; G01C 15/002; G01S 3/7865
USPC ........ 348/159, 222.1, 340, 49, 82, 135, 169, 348/614, 211.4; 73/865.8; 250/559.29, 250/559.38; 356/615, 141.4, 614; 700/259; 901/47
See application file for complete search history.

(56) References Cited

U.S. PATENT DOCUMENTS

| | | | |
|---|---|---|---|
| 5,305,356 A | 4/1994 | Brooks et al. | |
| 5,434,614 A | 7/1995 | Dainty | |
| 5,633,717 A * | 5/1997 | Baldur | G01B 11/026 250/559.29 |
| 6,121,999 A * | 9/2000 | Schaack | A61B 1/00147 348/135 |
| 6,259,474 B1 * | 7/2001 | Sera | H04N 7/18 348/82 |
| 6,966,754 B2 | 11/2005 | Wobben | |
| 7,009,698 B2 | 3/2006 | Drost et al. | |
| 7,013,203 B2 | 3/2006 | Moore et al. | |
| 7,075,634 B2 | 7/2006 | Uezono et al. | |
| 7,345,757 B2 | 3/2008 | Penza | |
| 7,448,271 B2 | 11/2008 | Duncan et al. | |
| 7,640,810 B2 | 1/2010 | Kennedy et al. | |
| 7,859,655 B2 * | 12/2010 | Troy | G01C 1/04 348/169 |
| 8,024,144 B2 | 9/2011 | Kludas et al. | |
| 8,044,991 B2 | 10/2011 | Lea et al. | |
| 8,171,809 B2 | 5/2012 | Fritz | |
| 8,179,078 B2 | 5/2012 | Sidman | |
| 8,251,599 B2 | 8/2012 | Chapman | |
| 8,261,599 B2 | 9/2012 | Jeffrey et al. | |
| 8,265,885 B2 | 9/2012 | George | |
| 8,270,667 B2 | 9/2012 | Fritz et al. | |
| 8,276,286 B2 | 10/2012 | Bailey et al. | |
| 8,277,183 B2 | 10/2012 | Qu | |
| 8,295,585 B2 | 10/2012 | Wienand et al. | |
| 2007/0039390 A1 | 2/2007 | Duncan et al. | |
| 2008/0136626 A1 | 6/2008 | Hudson et al. | |
| 2008/0179115 A1 | 7/2008 | Ohm | |
| 2009/0010285 A1 | 1/2009 | Dubois et al. | |
| 2009/0138233 A1 | 5/2009 | Kludas et al. | |
| 2009/0153656 A1 | 6/2009 | Sharanova | |
| 2009/0266160 A1 | 10/2009 | Jeffrey et al. | |
| 2010/0103260 A1 | 4/2010 | Williams | |
| 2010/0111489 A1 * | 5/2010 | Presler | H04N 5/225 386/278 |
| 2010/0183197 A1 | 7/2010 | Aikawa et al. | |
| 2011/0046917 A1 | 2/2011 | Lippuner | |
| 2011/0090110 A1 | 4/2011 | Tralshawala et al. | |
| 2011/0205348 A1 | 8/2011 | Fritz et al. | |
| 2011/0206511 A1 | 8/2011 | Frydendal | |
| 2011/0288817 A1 | 11/2011 | Von Mutius et al. | |
| 2012/0007982 A1 | 1/2012 | Giuffrida | |
| 2012/0038901 A1 | 2/2012 | McKaughan et al. | |
| 2012/0136630 A1 | 5/2012 | Murphy et al. | |
| 2012/0300059 A1 | 11/2012 | Stege | |
| 2012/0327187 A1 | 12/2012 | Troy et al. | |
| 2013/0002829 A1 | 1/2013 | Soerensen | |
| 2013/0003071 A1 | 1/2013 | Mamidipudi | |
| 2013/0054029 A1 * | 2/2013 | Huang | B25J 5/005 700/259 |
| 2013/0194412 A1 * | 8/2013 | Hatcher | F01D 21/003 348/82 |
| 2016/0287198 A1 * | 10/2016 | Abramovich | A61B 6/105 |

FOREIGN PATENT DOCUMENTS

| | | |
|---|---|---|
| WO | 2008092461 A2 | 8/2008 |
| WO | 2011113402 A1 | 9/2011 |
| WO | 2012003372 B1 | 1/2012 |
| WO | WO2012003372 | 1/2012 |
| WO | 2012081793 A1 | 6/2012 |
| WO | 2012145780 A2 | 11/2012 |

* cited by examiner

REMOTE VISUAL INSPECTION SYSTEM AND METHOD

CROSS-REFERENCE TO RELATED APPLICATIONS

This application is a National Entry Application of PCT application no CA2013/050466 filed on Jun. 18, 2013 and published in English under PCT Article 21(2), which itself claims benefit of U.S. provisional application Ser. No. 61/661,875 and Ser. No. 61/660,935, filed on Jun. 20, 2012 and Jun. 18, 2012 respectively. All documents above are incorporated herein in their entirety by reference.

FIELD OF THE INVENTION

The present invention relates to inspection of structures, like wind turbine blades, buildings, bridges, barrages. More specifically, the present invention is concerned with a method and a system for remote visual inspection of a wind turbine.

BACKGROUND OF THE INVENTION

There are many situations in which it is desirable to inspect inconveniently located structures.

For examples, the blades of wind turbines need to be inspected regularly to ensure that they are repaired or replaced when damaged. However, these blades are typically located at the top of relatively tall towers. In-person inspection in which a human climbs in the tower to visually or, with the help of equipment, inspects the blades is relatively time-consuming and can also be a relatively dangerous task. There exist prior art methods in which equipment is lifted at the required height so that the blades can be inspected. However, the lifting equipment is typically relatively expensive and relatively difficult to operate. Also, in many cases, the inspection equipment is not stably lifted, which may complicate the inspection procedure, and which also may cause damages to the wind turbine or the equipment if errors in control of the lifting equipment are made.

There exists a need in the art for a method and a system for remote inspection of structures such as wind turbines, buildings, bridges and barrages for example.

The present description refers to a number of documents, the content of which is herein incorporated by reference in their entirety.

SUMMARY OF THE INVENTION

More specifically, in accordance with the present invention, there is provided a system for remote visual inspection of a target surface of a structure, comprising a multi-axis assembly; a combination of dynamic digital video cameras and optic supported by said multi-axis assembly; and a controller connected to the cameras and the multi-axis assembly; wherein the multi-axis assembly comprises a turret along a vertical axis, the turret being connected at a top part thereof to a first arm extending along a roll axis, the first arm being connected to a second arm along a pitch axis, the cameras and optic being carried by the second arm.

There is further provided a method for remote visual inspection of a target surface of a structure, comprising positioning an inspection unit at a fixed location, the inspection unit comprising a combination of dynamic digital video cameras and an optic supported by a pitch axis of a multi-axis assembly comprising three moveable axis, including a vertical axis, a roll axis connected to the vertical axis, and the pitch axis, the pitch axis being connected to the roll axis; and a controller connected to the combination and the multi-axis assembly; adjusting the positioned inspection relative to the target surface; calibrating a target surface of the structure; taking images of the calibrated surface of the structure, each image including at least position data of the target surface and angular data of the inspection unit; and detecting, in the images, defects on the target surface, and, from the position data and angular data, positioning the defects on the target surface and determining the dimensions of the defects.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

A system according to an aspect of the present invention will first be described in relation to FIGS. 1 to 4.

Figure 1:
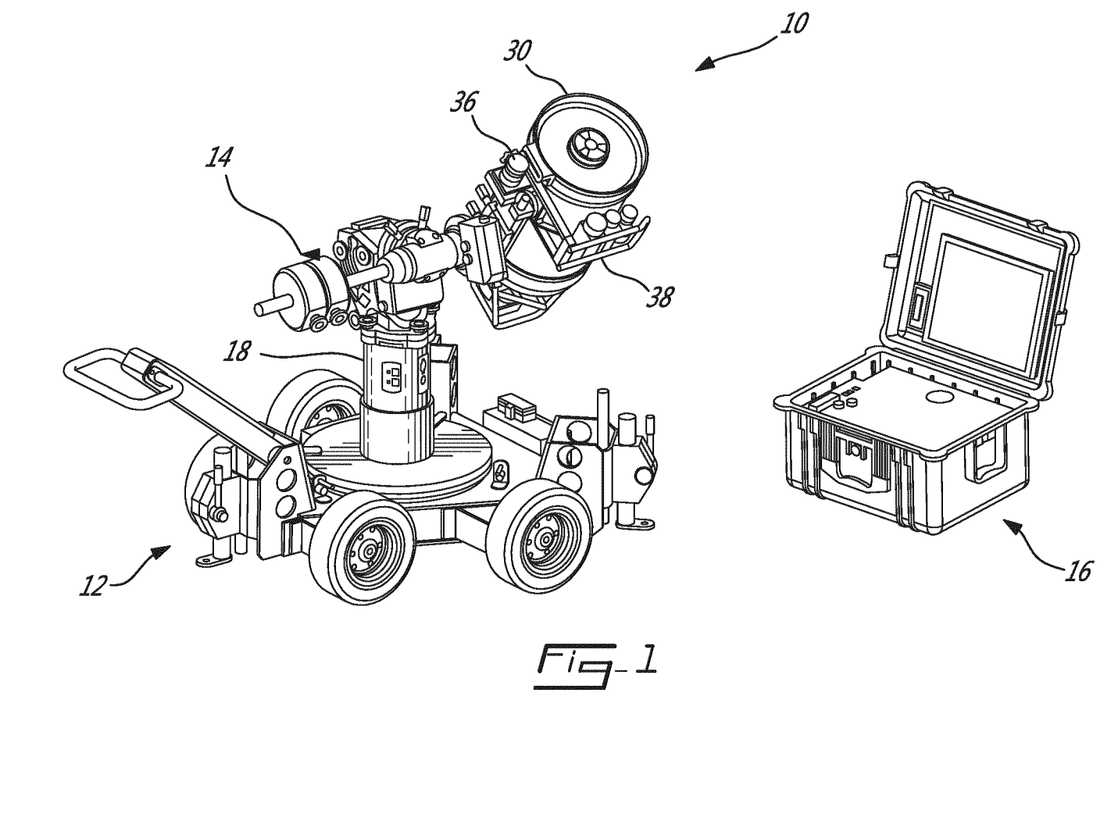
FIG. 1 is a first perspective view of a system according to an embodiment of an aspect of the present invention.
Figure 2:
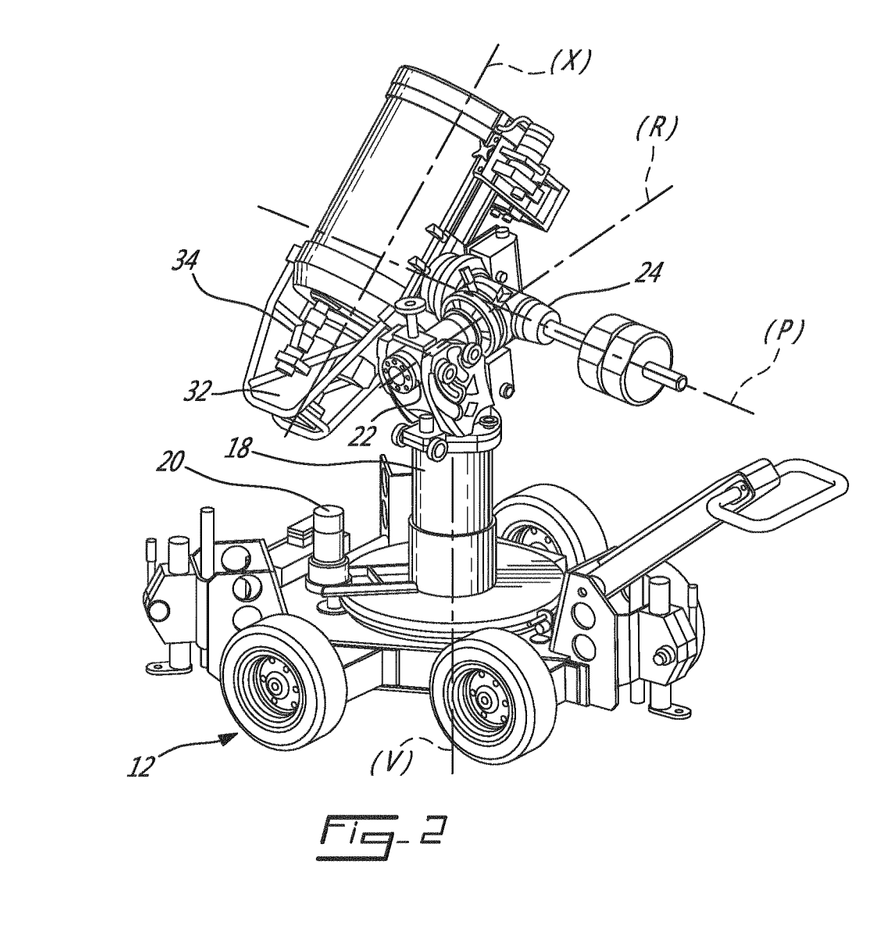
FIG. 2 is a perspective view of the an inspection unit according to an embodiment of an aspect of the present invention.

The system 10 generally comprises an inspection unit 14, supported, on a base 12 for example, through a multi-axis assembly, and a controller 16.

The inspection unit 14 comprises a combination of dynamic digital video cameras and powerful optic selected for high sensibility and light gathering capacity, and a motorized focusing unit 34.

The dynamic digital video cameras include a high resolution camera 32 and a wide view camera 36, the wide view camera 36 being used to help navigate the visual space when aligning the optical axis (X) of the inspection unit 14 to a surface to be inspected as will be discussed hereinbelow in relation to FIG. 6 for example. The cameras 32, 36 are selected to allow a full and separate control of each image parameters, i.e. at least contrast and exposure. The high resolution camera 32 is selected to have a resolution of about 10 Megapixels or more, with a video mode capacity, dual speed modes, and high frame per second for video-like imaging and slower full resolution imaging for quality still shots.

The optic 30 is selected in higher end light gathering optics, such as telescopes with large diameters, i.e. typically 9 inches and more, with enhanced light gathering capacities. It also comprises appropriate focal length adapters used to achieve good image resolution, depending on specific optical tube and sensor combinations used.

The inspection unit 14 further comprises a range measurement device 38. The range measurement device 38 provides a range-measurement beam aligned with the optical axis (X) of the inspection unit 14 and enables measurement of the distance between the inspection unit 14 and a target surface to inspect.

The multi-axis assembly allows orienting the inspection unit 14 in relation to target surface according to three axes.

The multi-axis assembly comprises a turret 18 along a vertical axis (V) mounted on the base 12, with its motor 20, supporting by moveable joint a first arm 22, the first arm 22 supporting by moveable joint at a second end thereof a second arm 24. The optic 30 and the cameras 32, 36 are carried at an end of the arm 24. Such multi-axis assembly thus provides three moveable axes: a vertical axis (V), a roll axis (R) and a pitch axis (P), with a minimized coupling between the optical axis (X) of the inspection unit 14 and the three moveable axes by providing that the optical axis (X) be oriented by adjusting the roll angle about the roll axis (R).

As will be described hereinbelow in relation to the method (FIG. 5), if lateral movement is required to place the target structure in the center of the inspection system 14's line of sight (X), the vertical axis (V) can be rotated left and right and provide panning effect about the target surface. The roll angle revolving around the roll axis (R) of the inspection unit 14 can be aligned to the longitudinal axis of the target surface, allowing the camera 32 to take pictures of the target surface orthogonally to the target surface (see angle δ FIG. 3 for example). The pitch angle revolving around the pitch axis (P) can be used to scan the target surface and take pictures orthogonal to the axis of movement of the structure to be inspected (see angle β FIG. 4 for example).

Each movement axis is motorized, with or without reduction, control sets, directly operated or computer operated. Small movement resolution and steady slow motor speed capacity is required. The motor driving each axis is provided with motion sensors. All featuring motion measurements with feedback are directed to the controller 16.

The controller 16 controls orientation of the inspection unit 14, allows visualizing image data collected by the camera 32, storing and processing data received from the camera 32 and from the position sensors.

Figure 5:
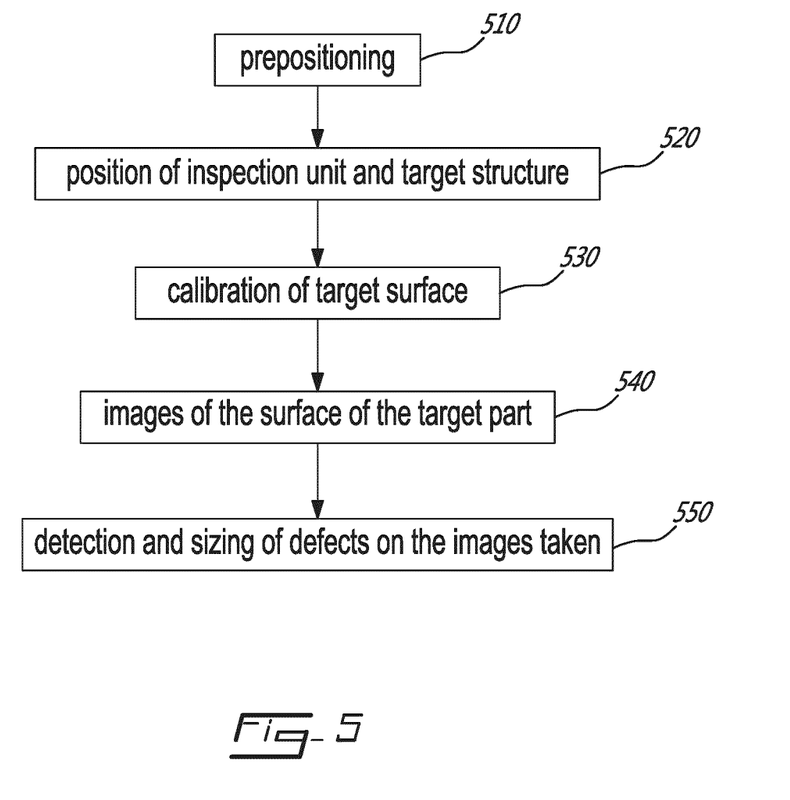
FIG. 5 is a flowchart of a method according to an embodiment of an aspect of the present invention.

The system 10 can use angular data collected by the motion sensors of each motorized axis, for example the pitch axis (P), the roll axis (R) and the vertical axis (V), and distance measurements provided by the range measurement device 38 to 1) calculate planes of references, positions, and locations on inspected targets and to 2) calculate size, position and orientation of geometries on pictures taken on inspection targets, as will be discussed hereinbelow in relation to FIG. 5 (step 550).

The base 12 may be a ground-based carriage, or a carriage fixed to a permanent base or a carriage mobile on wheels as illustrated for example, or tracks or pads for example. The base 12 may be fitted with a leveling mechanism 40. The base 12 may also be fitted with a handle 10 to allow for ground maneuvering when fitted with mobility devices such as wheels, tracks or pads for example.

The controller may be packaged and carried in a control station, under the form of an independent box for example or fixed, i.e. built-in, to the inspection unit 14. The control station comprises a keyboard and computer interface with a display for viewing images taken by the camera 32, as well as other control functions directly related to the operation of the inspection unit 14, such as emergency button allowing stopping movements along the axis of multi-axis assembly if needed, focusing control etc. . . . . . Some functions may also be electrically controlled.

An embodiment of a method of the present invention will now be described in relation to FIGS. 5 to 10, in the case of a horizontal-axis wind turbine (S). The horizontal-axis wind turbine (S), as illustrated for example in FIGS. 3 and 4, for example, comprises a tower (T) having a height (H) along a generally vertical axis between its upper end and its base on a support surface (U), a nacelle (N) at the upper end and a rotor (R) coupled to the nacelle (N) and including a rotatable hub (H) and blades 100, 102, 104 coupled to and extending outward from the hub (H).

For a given structure to be inspected, a position for installing the inspection unit is selected, taking into account a number of environmental parameters including geographical parameters and light and wind parameters (step 510).

Light parameters include the position of the sun, which determines the angle of light incident on the structure, and of clouds, which may generate variable shading and overexposure.

Figure 3:
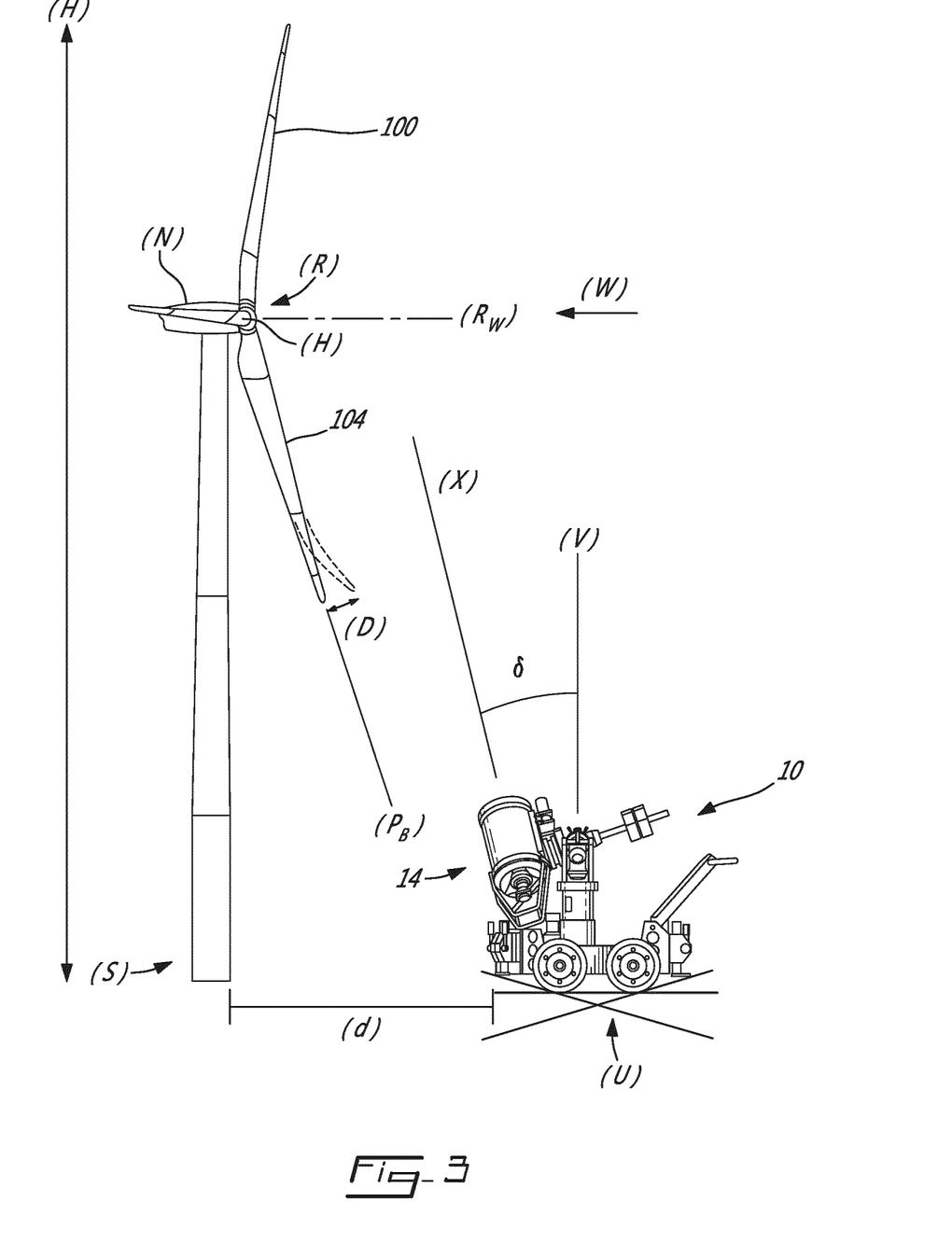
FIG. 3 is a plan view showing alignment of the optical axis of the inspection unit with a longitudinal axis of a target to be inspected according to an embodiment of an aspect of the present invention.

Wind parameters include the direction of the wind, which determines the position of the rotation axis of the rotor (R) in case of a horizontal axis wind turbine: as illustrated in FIG. 3 for example, as wind strikes the blades from a direction (W), the rotor (R) is rotated about an axis ($R_W$).

Based on the direction of the wind and of the rotation axis of the rotor (R) axis, a position for the inspection unit is selected so that the inspection unit 14 has a clear view of upwind and downwind surfaces of the target blade.

Geographical parameters include the available space and ground surface as well as accessibility about the structure and the configuration of the land, i.e. inequalities of elevation of the surroundings. These geographical parameters determine suitable locations for the inspection unit, and thus the distance between the inspection unit and the structure to be inspected Thus, as illustrated for example in FIGS. 3 and 4, the inspection unit 14 is positioned at a distance (d) from the base of the tower (T). The distance (d) may vary, depending on the geographical parameters discussed above, which dictate accessibility to the structure, from 0, i. e. the inspection unit 14 being positioned at the base of the structure and the optical axis (X) of the inspection unit pointing generally vertically.

When the inspection unit 14 is thus positioned on an identified access path in a position allowing a clear view of upwind and downwind surfaces of the target blade so that structure to be inspected is ideally positioned so that the right side of the nacelle (N), which presents the downwind surface, is visible from the access path, with the rotor (R) at the right handside relative to the tower (T) (see FIG. 3 for example), the target surface and the inspection unit 14 are adjusted (step 520).

Figure 7:
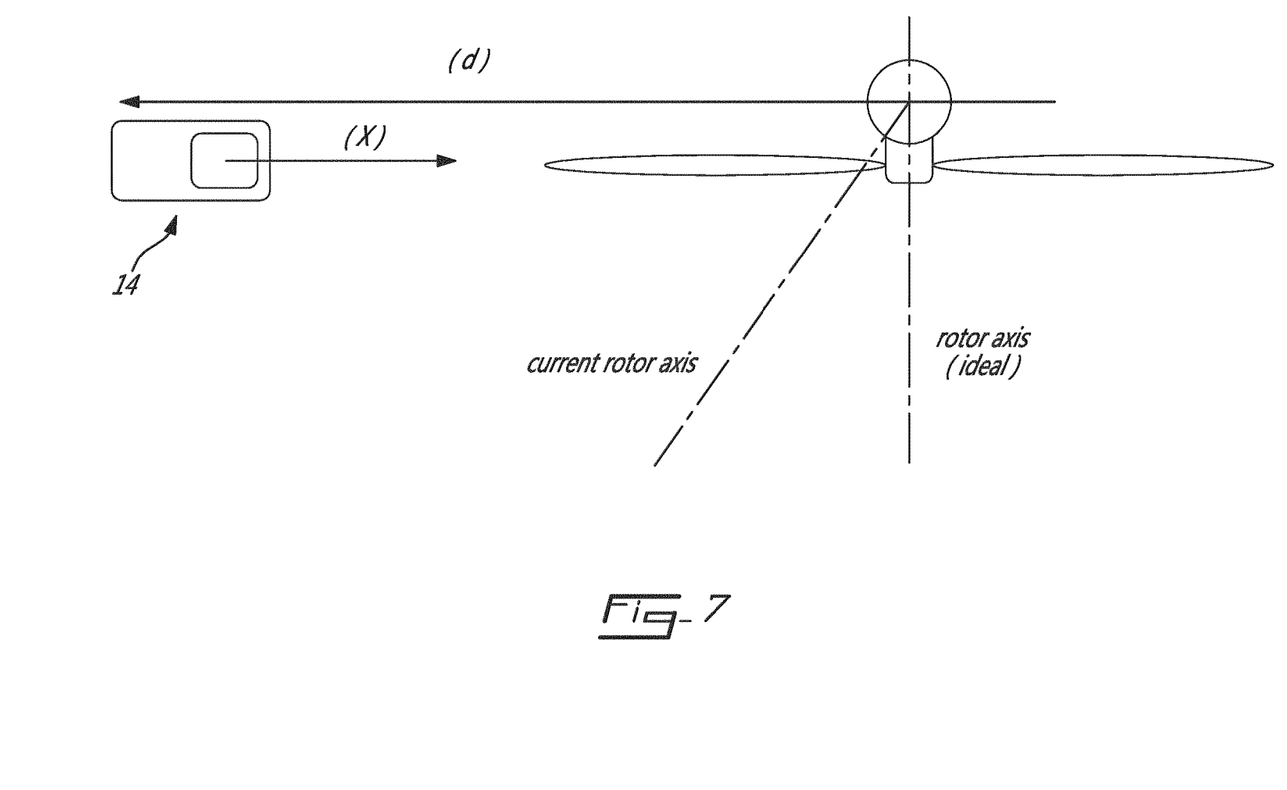
FIG. 7 shows positioning of the inspection unit relative to the target structure according to an embodiment of an aspect of the present invention.
Figure 8:
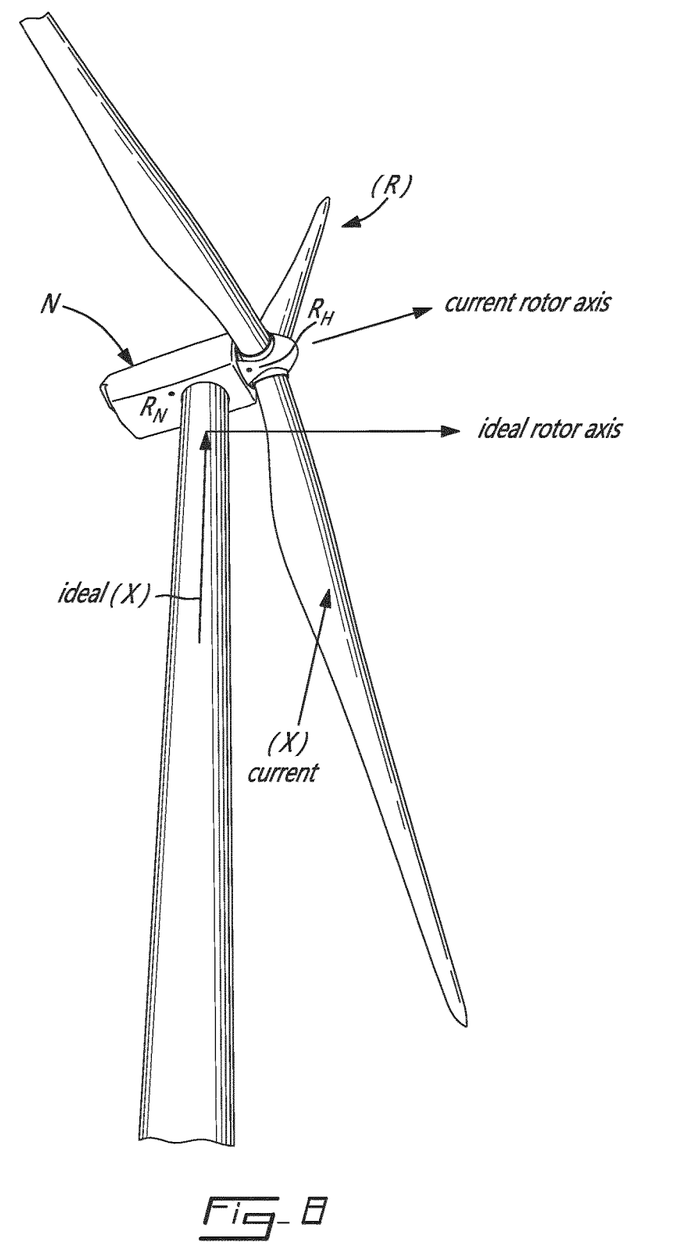
FIG. 8 shows determination of the normal position of a target blade relative to the optical axis (X) of the inspection unit by considering a reference point $R_N$ on the nacelle (N) and a reference point $R_H$ on the hub (H), according to an embodiment of an aspect of the present invention.

As illustrated in FIGS. 7 and 8, an ideal positioning places the inspection unit 14 with its optical axis (X) generally perpendicular to the rotor axis.

In case of a windmill as illustrated herein, adjustment may involve positioning of the target part.

Figure 6A:
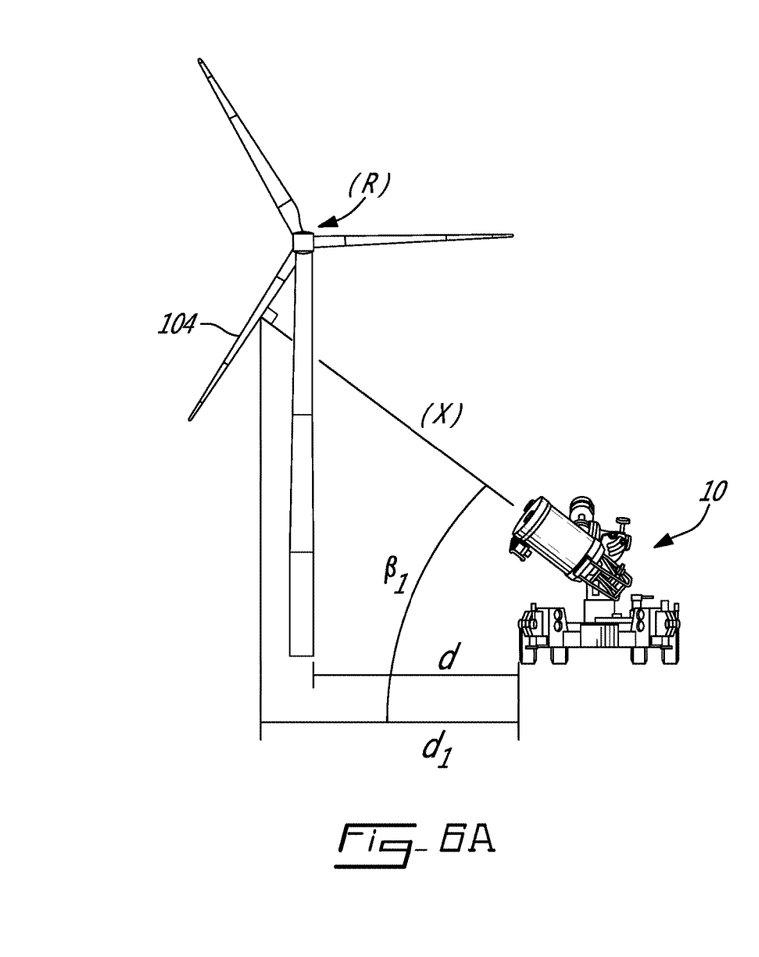
FIGS. 6a) and b) show variation of the pitch angle β of the inspection unit as the distance between the inspection unit and the target varies according to an embodiment of an aspect of the present invention.
Figure 6B:
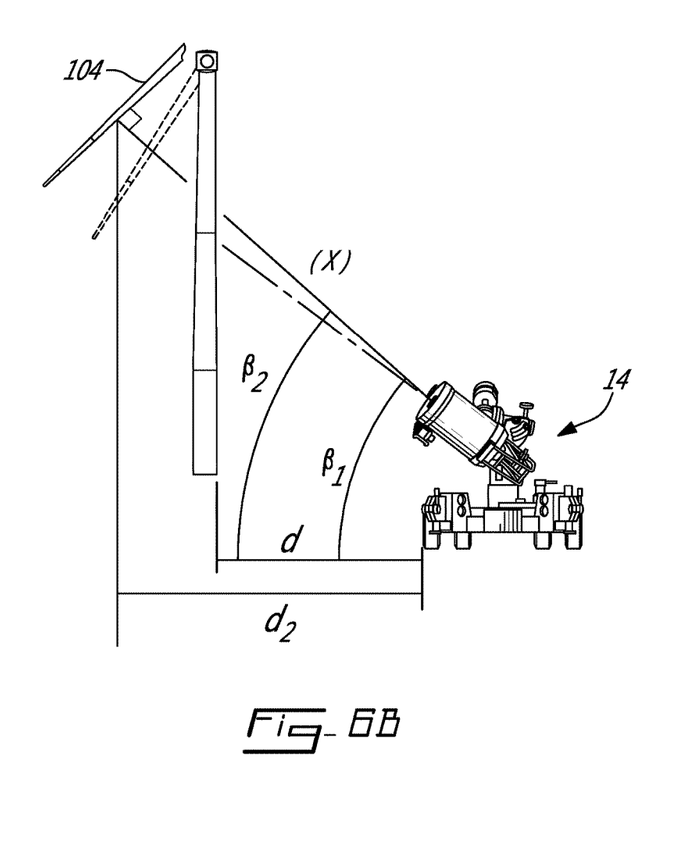

With the nacelle (N) and the rotor (R) stopped, first, for a given roll angle δ of the inspection unit to reach the normal to the target surface, the pitch angle β of the inspection unit varies as the distance between the inspection unit 14 and the target varies (see ($d_1$) and ($d_2$) in FIG. 6). The minimum distance (d) between the base of the structure and the inspection unit is determined by the target spatial resolution. Secondly, for a given roll angle δ of the inspection unit and a given distance (d) between the base of the structure and the inspection unit, when the elevation of the inspection unit relative to the structure rises or lowers, the pitch angle β of the inspection unit varies accordingly.

As illustrated in FIG. 8, the normal position of the target blade relative to the optical axis (X) of the inspection unit 12 is determined by, considering a reference point $R_N$ on the nacelle (N) and a reference point $R_H$ on the hub (H), rotating the rotor (R) to physically align these two reference points $R_N$ and $R_H$. The rotation of the rotor (R) is then stopped. The nacelle may then be further adjusted, by left or right pivot movements according to current geographical parameters discussed hereinabove; in parallel, the inspection unit is oriented so that the optical axis (X) points to the target surface by aligning the pitch axis of the inspection unit along the longitudinal axis of the target blade by adjusting the roll angle of the inspection unit.

Such positioning selection allows minimizing and eliminating further need for pivoting the nacelle (N), by only pivoting the target blade about its pitch axis ($P_B$) if necessary, within its limit switch, when optimizing the light conditions on the target blade, and thus results in shorter downtime. For example, the surface of the blade to be inspected is positioned according to the light conditions and the shooting angle of the camera of the inspection unit to minimize overexposure and also shadow effects on the target surface, thereby minimizing extreme contrasts.

This relative positioning of the inspection unit 14 and of the nacelle (N) allows taking images under the blade (see FIG. 4 for example), i.e. in the downwind side or shadowed part, even in low light conditions due the combination of cameras and optic described hereinabove, thus avoiding overexposure and lengthy images adjustments.

The angle between the optical axis (X) of the inspection unit 14 and the axis of the rotor may vary from the normal, and be comprised in a range between about 0 and 90°, for example between about 60 and 90°, depending on the geographical parameters discussed hereinabove.

In case of a target structure without mobile element, such as a building façade for example, adjustment positioning (step 520) does not involve positioning of the target part.

In case of a structure on a slope and an inspection unit 12 that can only be positioned downhill therefrom, the angle between the optical axis and the target surface may be comprised between 90 and 120° (see "current" configuration versus "ideal" configuration in FIG. 8).

Figure 4:
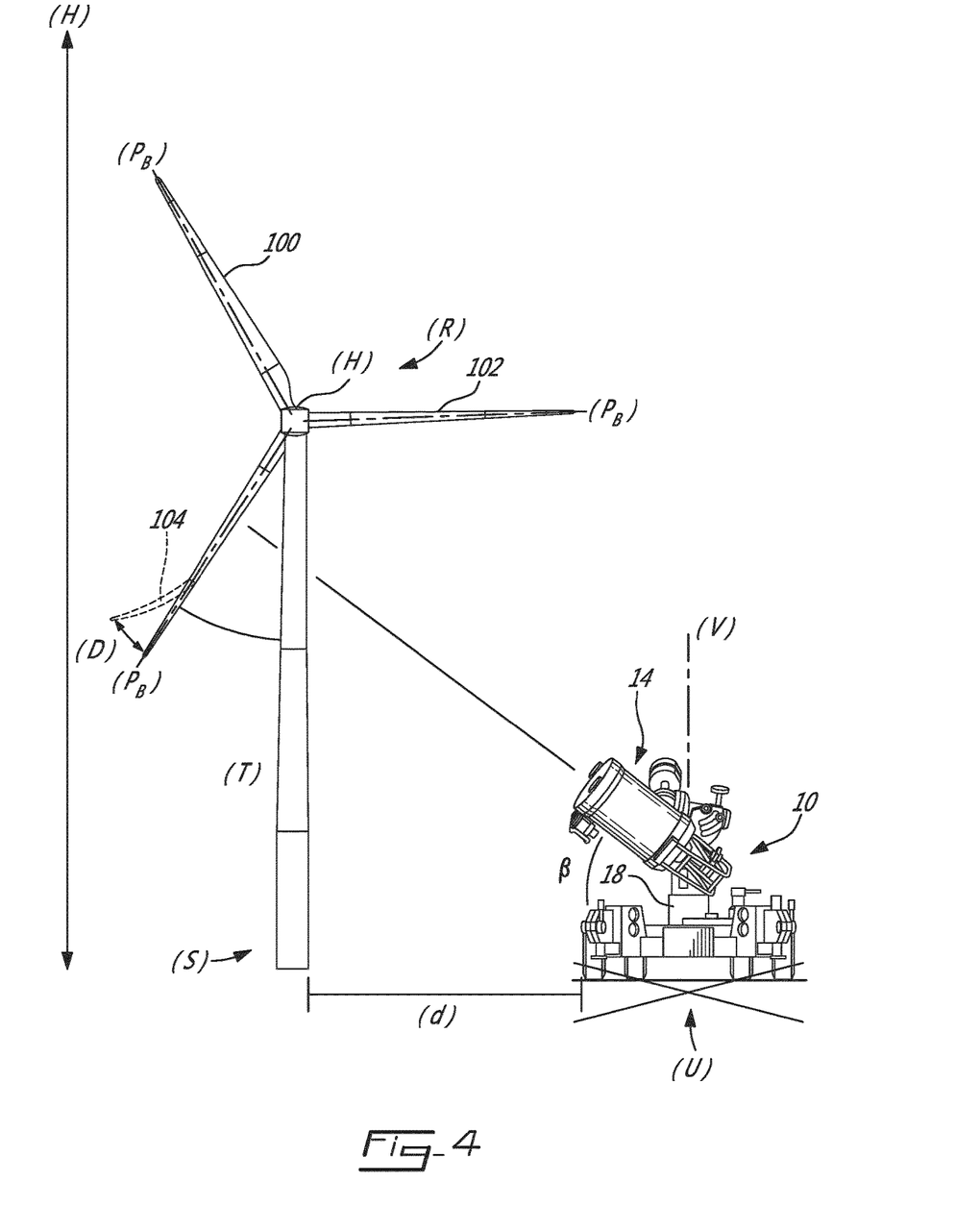
FIG. 4 is a side planar view of the system of FIG. 3 showing alignment of the optical axis of the inspection unit with the normal to a target surface according to an embodiment of an aspect of the present invention.

As shown in FIGS. 3 and 4 for example, with the rotor (R) at stop placed in such a way that the blade 104 is in full view of the system 10 as discussed hereinabove, the system 10 is oriented by adjusting the roll angle δ about the roll axis (R) of the inspection unit 14 for alignment of the optical axis (X) parallel to the longitudinal axis ($P_B$) of the target surface 104 as seen in a planer view (FIG. 3) and alignment of the optical axis (X) generally along the normal to the target surface in a lateral planer view (see FIG. 4).

Figure 9:
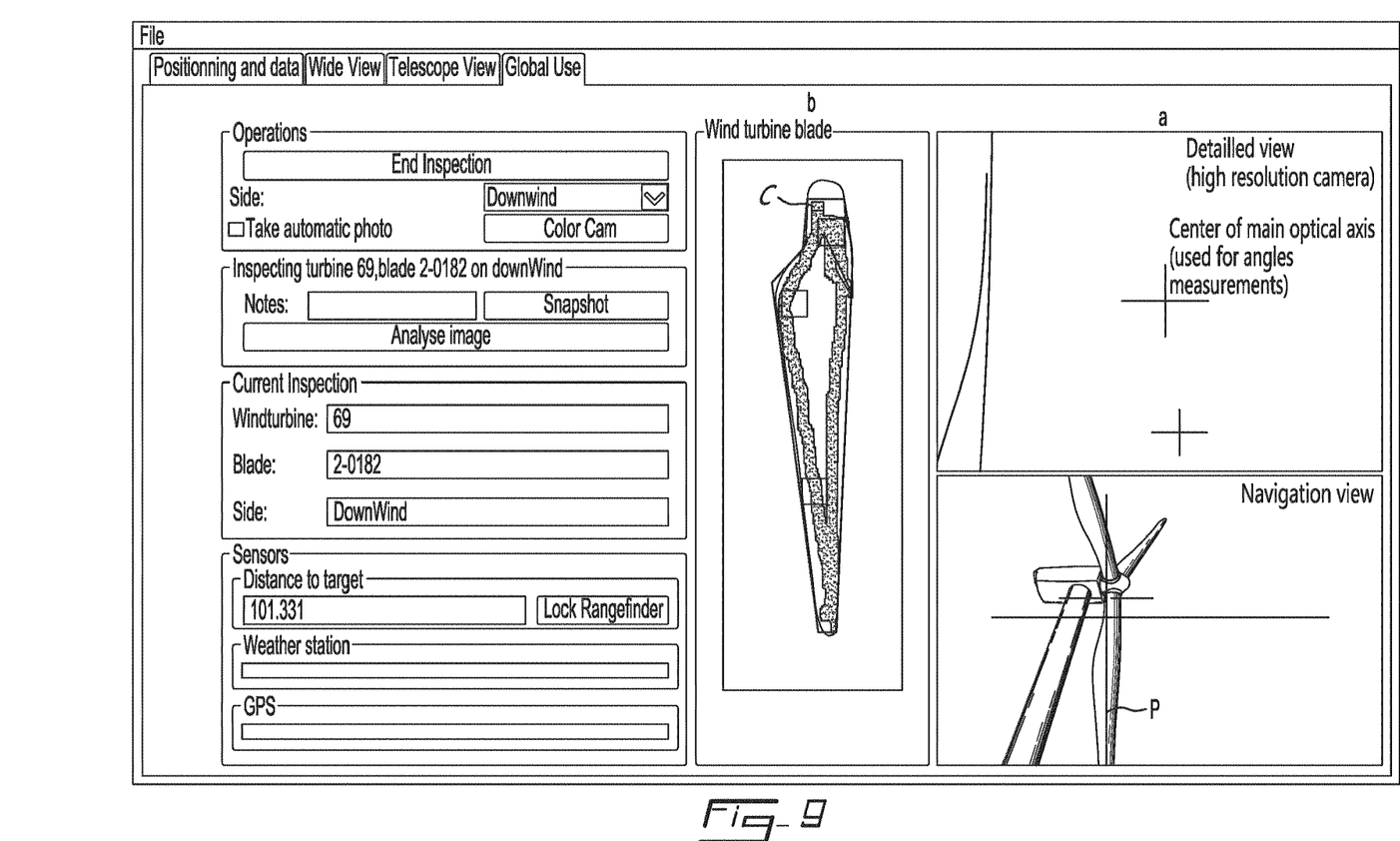
FIG. 9 shows an interface of a control station of a system according to an embodiment of an aspect of the present invention.

In step 530, center axis calibration between the two cameras is made by pointing the cameras, i.e. the optical axis (X), to a reference point of the target, such as for example a tip of a blade, and using digitally generated lines, including a vertical line and a horizontal line, overlaid over the camera image on the computer interface of the control station. These lines are moveable on the screen and can be moved in the navigation camera 36's window to align with the reference point on the target (see FIG. 9a). In FIG. 9a, axis (P) corresponds to pitch movement axis and is aligned in space by action about the roll axis (R).

Images of the target surface are taken by the camera 32 of the inspection unit. The camera scans the target blade, along its longitudinal direction, from its root at the hub (H) to its tip for example, which allows shooting first the root part generally bearing the serial number of the blade, as many times as required by its width depending of the surface size of each image, as the target blade is fixed in a vertical plane (step 540) (see FIG. 4). In FIG. 9b, the shaded part indicates locations on the blade that have been scanned. The squares shown in FIG. 9b represent the size of images taken on the blade.

Images of the target surfaces 104 are taken generally orthogonal to the target surface 104. When the optical axis (X) of the inspection unit 14 is generally aligned along the normal to the target surface as described hereinabove in relation to step 520, image distortion over the whole surface of the target blade is minimized and image size repeatability and image resolution for the entire inspection plane is improved while need for focus and image adjustments is minimized, this unloading the system or the operator and speeding up the inspection process.

The scanning by the camera is done for a fixed position of the blade in the vertical plane. However, even when rotation of the rotor (R) is stopped, the blades may be subjected to deflection and/or oscillations (see arrow D in FIGS. 3 and 4 for example) and in practice, the blade is in constant 3D motion due to wind. The light conditions typically also vary during the scan of the surface.

Thus, the inspection unit, which is positioned at a fixed distance (d) from the structure, continuously adjusts the focal distance. For example, the inspection unit adjusts the focal distance through its focusing unit 34, activated through active calculation in the controller 16 fed by range data provided by the range measurement device 38. The range measurement device 38, which, aligned to the main optical axis (X) of the inspection unit 14, i.e. the shooting angle of the camera 32 of the inspection unit, measures in real time the distance between the fixed inspection unit 14 and the moving target. The controller 16 thus adjusts to the motions of the blade using the wide view camera 36 when required. The focus adjustment may thus be made based on the focal distance of the optic and of the distance between the optic and the target part, but also based on image quality by image processing in case of blurred images for example.

The inspection unit also adjusts to the varying light conditions by controlling exposure and contrast of the camera 32.

For inspecting a given blade of a wind turbine, the blade may be rotated along its own longitudinal axis, coincident with its pitch axis ($P_B$), to allow vision of all sides thereof by the inspection unit 14 in successive steps as described hereinabove.

The combination of two cameras, including a high definition camera and the wide view camera for example as described hereinabove, allows taking detailed views of the blades surface, for example images covering 1 m by 1 m of target surface with at least 10 Megapixels resolution. Each such image includes the corresponding positioning data of the inspection unit in terms of its vertical, roll and pitch angles, data from the range finder, data of the geographical and light and wind parameters, and position data of the corresponding part of the target surface. Thus, each picture is geo-referenced.

In step 550, the images of the surface are processed to detect defects of the target part by viewing defects on its surface (step 550), from hairline cracks to open cracks. In step 550, the exact position of defects of the imaged anomaly is determined in the longitudinal axis and in the transverse direction of the target blade and their dimensions, length and width, are precisely determined from the images taken and the corresponding angular data of the inspection unit 12.

The optic 30 used allows a strong light gathering capacity, for example using a Schmidt-Casgrain configuration. Imaging can be done in color, or in greyscale, which involves a simpler set up and fewer adjustments.

A full and separate control of exposure and contrast of the images is performed. A first step of image configuration for defect detection comprises adjusting the exposure to avoid overexposure, i. e blinded image. Simultaneously, the focus is adjusted, manually or automatically, for image sharpness. Secondly, contrast is adjusted to provide darker than normal images which allow revealing slight texture coloring or tone variations. A proper adjustment completely shadows thin voids, i.e. cracks on the surface, and reveals grey tone differences on white blade surfaces, without causing image overexposure, thereby allowing revealing even slightest curvatures on the surface geometry and material bucking and cracking, as well as hairlines cracks as small as 1 mm. Other digital image processing techniques such as rasterization, light normalization, using histograms, for example, can be used in conjunction.

The angular data collected by the motion sensors of each motorized axis, the pitch axis (P), the roll axis (R) and the vertical axis (V), and distance measurements provided by the range measurement device 38 are used 1) calculate planes of references, positions, and locations on inspected targets and to 2) calculate size, position and orientation of geometries on pictures taken on inspection targets.

Figure 10:
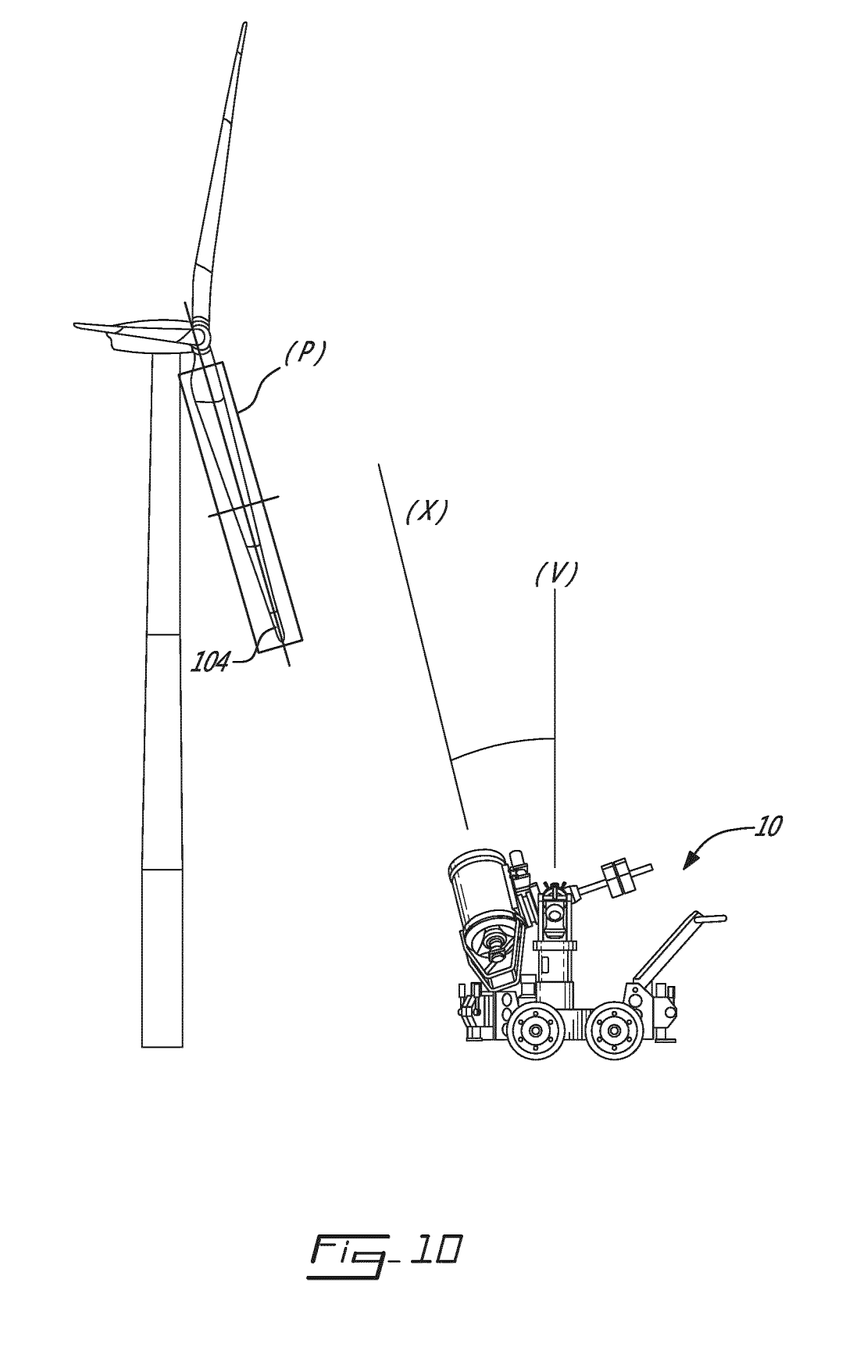
FIG. 10 shows determination of a virtual plane (P) associated with a target, according to an embodiment of an aspect of the present invention.

The 3 dimensional position of the blade in space in relation to the ground (i. e., the fixed inspection unit, with its angles) may be determined by using angles measurements of the position of the blade root and of the blade tip to determine the blade's longitudinal axis, and the leftmost and rightmost positions of the blade at a location on the blade to determine a transverse axis the blade, the longitudinal axis and the transversal axis defining a virtual plane (P), referred to as the inspection plane, which is defined for each inspection (see FIG. 10).

Position along the longitudinal direction of the blade is calculated by resolving trigonometry calculations for example, using a constant, i. e. the blade length, and variables, i.e. the distance and angle to the blade root and the distance and angle to the blade tip. Position along transverse direction of the blade is calculated using a constant, i. e. the blade maximal width, and a variable, i.e. the width between the right side and the left of the blade at this position at this position measured from with the angular sensors of each axis of the inspection unit) and the range measurement device.

The present system and method may be easily deployed and operated by a small number of operators. It allows inspecting a structure without the need for any operator climbing the structure for actual inspection or installing support equipment.

As people in the art will appreciate, the present system and method allows remote inspection of a structure such as wind turbine blades, buildings, bridges, barrages, etc., from a distance, i.e. independently of land conditions or access in the immediate vicinity of the structures for example, without contact with the structure, and in a range of climatic conditions.

The present method and system allows, based on imaging, from a distance and without contact, outer surfaces of structures, to assess the state of the structure by detecting defects on these surfaces. These defects are precisely localized on the structure and sized, from the images.

The scope of the claims should not be limited by the preferred embodiments set forth in the examples, but should be given the broadest interpretation consistent with the description as a whole.

The invention claimed is:

1. A system for remote visual inspection of a target surface of a structure, comprising:
   a multi-axis assembly;
   a combination of two cameras and optic having an optical axis and supported by said multi-axis assembly; and
   a controller connected to said cameras and said multi-axis assembly;
   wherein said multi-axis assembly comprises a vertical axis, a roll axis and a pitch axis;
   said controller controlling rotation of the vertical axis to place the target surface in the line of sight of the system; aligning the roll angle about the roll axis to a longitudinal axis of the target surface of the structure; and revolving of a pitch angle around said pitch axis for scanning the target surface of the structure; thereby allowing the cameras to take pictures of the target surface orthogonally to the target surface and along the longitudinal axis of the target, the system being positioned at a fixed distance from the structure.

2. The system of claim 1, wherein said combination comprises a high resolution dynamic digital video camera and a light gathering optic.

3. The system of claim 1, wherein said combination comprises a high resolution dynamic camera, a wide view camera and a light gathering optic.

4. The system of claim 1, further comprising a range measurement device aligned with the optical axis, said controller receiving data from said range measurement device.

5. The system of claim 1, wherein each axis is provided with motion sensors, said controller receiving data from said motion sensors.

6. The system of claim 1, further comprising a range measurement device, each axis being provided with motion sensors, said controller receiving angular data from said motion sensors and distance measurements from said range measurement device, said controller using said angular data collected by the motion sensors of each axis and said distance measurements provided by the range measurement device to calculate planes of references, positions, and locations on the target surface of the structure and to calculate size, position and orientation of geometries on pictures taken on said target surface by said cameras.

7. The system of claim 1, wherein said vertical axis, roll axis and pitch axis have a minimum coupling with the optical axis.

8. The system of claim 1, wherein said controller controls orientation of the cameras and optic.

9. The system of claim 1, wherein said pitch angle about said pitch axis being also adjustable according to a distance between a base of the structure and the system and to an elevation of the system relative to the structure.

* * * * *